US012667679B2

(12) United States Patent (10) Patent No.: US 12,667,679 B2
Jung et al. (45) Date of Patent: Jun. 30, 2026

(54) ELECTRONIC SYSTEM

(71) Applicant: Presspart GmbH & Co. KG, Marsberg (DE)

(72) Inventors: Benjamin Jung, Pulheim (DE); Kyle Wilson, Düsseldorf (DE); Richard Turner, Lancashire (GB); Julian Hemy, Cheshire (GB); Inga Meyer, Düsseldorf (DE); Nicholas G. Lesniewski-Laas, Somerville, MA (US)

(73) Assignee: Presspart GmbH & Co. KG, Marsberg (DE)

( * ) Notice: Subject to any disclaimer, the term of this patent is extended or adjusted under 35 U.S.C. 154(b) by 980 days.

(21) Appl. No.: 17/431,304

(22) PCT Filed: Mar. 6, 2020

(86) PCT No.: PCT/EP2020/056011
§ 371 (c)(1),
(2) Date: Aug. 16, 2021

(87) PCT Pub. No.: WO2020/182655
PCT Pub. Date: Sep. 17, 2020

(65) Prior Publication Data
US 2022/0143333 A1 May 12, 2022

(30) Foreign Application Priority Data
Mar. 8, 2019 (EP) ..................................... 19161690

(51) Int. Cl.
*A61M 15/00* (2006.01)
*G16H 20/10* (2018.01)
(52) U.S. Cl.
CPC ........ *A61M 15/008* (2014.02); *A61M 15/003* (2014.02); *A61M 15/0045* (2013.01);
(Continued)

(58) Field of Classification Search
CPC .............. A61M 15/008; A61M 15/003; A61M 15/0045; A61M 2205/3375;
(Continued)

(56) References Cited

U.S. PATENT DOCUMENTS

| 8,807,131 B1 * | 8/2014 | Tunnell ............. A61M 15/0021 |
| | | 128/200.14 |
| 2003/0011476 A1 * | 1/2003 | Godfrey ........... G06K 19/07758 |
| | | 340/693.5 |

(Continued)

FOREIGN PATENT DOCUMENTS

| EP | 3363485 A1 | 8/2018 |
| GB | 2552539 A | 1/2018 |
| WO | WO-2015052519 A1 * | 4/2015 ............. A61B 5/087 |

OTHER PUBLICATIONS

European communication dated Sep. 17, 2019 in corresponding European patent application No. 19161690.3.
(Continued)

*Primary Examiner* — Brandy S Lee
*Assistant Examiner* — Tina Zhang
(74) *Attorney, Agent, or Firm* — Nields, Lemack & Frame, LLC

(57) ABSTRACT

An electronic system (1) comprises an electronic device (2) for gathering data from an inhaler (3) which is configured to dispense doses of a pharmaceutical formulation stored in a medicament reservoir. The system (1) further comprises an evaluation unit (9) being configured to receive and evaluate the gathered data in order to determine adherence to prescription data and/or to determine the number of doses having been dispensed or remaining in the inhaler (3) and a display (8) for visualizing the evaluated data. The electronic device (2) comprises a wireless interface (4) for receiving wireless data from the inhaler (3) via a wireless connection an input interface (5) for receiving manual input data and an
(Continued)

acoustic or visual interface (6, 7) for receiving acoustic or visual data of the inhaler (3). The evaluation unit (9) is configured to identify the gathered data as wireless, acoustic, visual or manual input data, identify the inhaler model from which the data was gathered across different manufactures, process and evaluate the gathered data and visualize the processed data on the display (8).

9 Claims, 2 Drawing Sheets

(52) U.S. Cl.
CPC ..... *G16H 20/10* (2018.01); *A61M 2205/3375* (2013.01); *A61M 2205/3553* (2013.01); *A61M 2205/3584* (2013.01); *A61M 2205/505* (2013.01); *A61M 2205/583* (2013.01); *A61M 2205/60* (2013.01)

(58) Field of Classification Search
CPC .. A61M 2205/3553; A61M 2205/3584; A61M 2205/505; A61M 2205/583; A61M 2205/60; A61M 2205/52; A61M 15/0065–0083; A61M 15/009; A61M 2205/3592; A61M 15/00; A61M 2205/581; A61M 2205/502; G16H 20/10; G16H 40/63; G16H 20/40; G16H 40/67; G16H 10/60; Y02A 90/10; A61B 5/4833
See application file for complete search history.

(56) References Cited

U.S. PATENT DOCUMENTS

| | | | | |
|---|---|---|---|---|
| 2004/0117062 | A1* | 6/2004 | Bonney | G16Z 99/00 |
| | | | | 700/244 |
| 2008/0077430 | A1* | 3/2008 | Singer | G16H 20/17 |
| | | | | 600/300 |
| 2009/0314292 | A1* | 12/2009 | Overfield | A61B 5/087 |
| | | | | 128/203.15 |
| 2011/0225008 | A1* | 9/2011 | Elkouh | A61M 15/008 |
| | | | | 726/4 |
| 2016/0106935 | A1* | 4/2016 | Sezan | A61M 15/0066 |
| | | | | 128/203.14 |
| 2017/0215480 | A1* | 8/2017 | Qiu | A24F 40/65 |
| 2018/0092595 | A1 | 4/2018 | Chen et al. | |
| 2018/0368197 | A1* | 12/2018 | Zeilingold | G16H 40/63 |
| 2019/0038854 | A1 | 2/2019 | Fuchs et al. | |
| 2019/0240430 | A1* | 8/2019 | Jackson | A61M 15/0065 |
| 2021/0110905 | A1* | 4/2021 | Häussermann | G06F 18/214 |

OTHER PUBLICATIONS

International Search Report and Written Opinion mailed May 12, 2020 in corresponding PCT application No. PCT/EP2020/056011.

* cited by examiner

ELECTRONIC SYSTEM

TECHNICAL FIELD

The present invention relates to an electronic system comprising an electronic device for gathering data from an inhaler which is configured to dispense doses of a pharmaceutical formulation stored in a medicament reservoir. The system further comprises an evaluation unit being configured to receive and evaluate the gathered data in order to determine adherence to prescription data and/or to determine the number of doses having been dispensed or remaining in the inhaler. Moreover, the system comprises a display for visualizing the evaluated data. The electronic device has a wireless interface for receiving wireless data from the inhaler via a wireless connection, an input interface for receiving manual input data and an acoustic or visual interface for receiving acoustic or visual data of the inhaler.

BACKGROUND OF THE INVENTION

Inhalers such as metered dose inhalers (MDIs), dry powder inhalers (DPIs) or soft mist inhalers are medication delivery devices which deliver a pharmaceutical formulation including one or more pharmaceutically active compounds to a human or other mammalian patient. Depending on the type of inhaler the pharmaceutical formulation is stored in different types of medicament reservoirs. For example MDIs or soft mist inhalers typically use canisters in order to store the pharmaceutical formulation. Blister strips or capsules are typically used in combination with DPIs.

The unit dose is expelled by the inhaler and is taken into the body of the patient on inhalation, via the nose or mouth. The pharmaceutical formulation is delivered to or via the respiratory tracts, notably to the lungs, of the patient on inhalation. The inhalers are typically used for the treatment of respiratory infections and disorders including respiratory tract infections, obstructive lung disease, inflammatory lung disease and chronic obstructive pulmonary disease. Asthma treatment is a particularly common use of the inhalers.

There has been a recent development towards the use of smart inhalers which not only allow electronic dose counting of the dispensed doses but also allow the implementation of additional functions such as monitoring functions or evaluation functions. Based on these additional functions a physician or the patient may for example monitor the frequency of dispensed doses and the point of time when these doses have been dispensed.

EP 3 363 485 A1 discloses a metered dose inhaler with an actuation housing and an electronic dose counter. Upon movement of a container from a rest position to an activation position in which an aerosol dose is released a single trigger member is actuated. Upon actuation the trigger member interacts with a switch generating an electrical signal that is transmitted to a circuit assembly. The metered dose inhaler may comprise a transmitting unit for wirelessly transmitting results processed by the circuit assembly. The results may be transmitted to a user's smartphone or any other electronic device.

Moreover, Cohero Health has developed a respiratory care platform and a corresponding app called BreatheSmart® by use of which data of a MDI may also be shared wirelessly via a smartphone. The BreatheSmart® platform can provide customized reminders, real-time alerts and updates on medication usage, as well as weekly and monthly summary reports. Patients can opt to share their data with family, caregivers and/or healthcare providers, with access via a web app on a secure, dedicated, HIPPA-compliant server.

However, only products provided by Cohero Health or by companies cooperating with Cohero Health such as inhalers with or without add-on devices to record and transmit data of an inhaler are capable to transmit data to the BreatheSmart® platform. If a patient uses multiple products, e.g. multiple inhalers, of different inhaler manufacturers which are not connectable to the same platform monitoring the administered doses as well as sharing and evaluating information with physicians is complicated.

It is an object of the present invention to provide an electronic system which provides simplified monitoring of inhaler data such as dose counts, allows simplified sharing of inhaler data with physicians and provides increased customer satisfaction. It is also an object of the present invention to provide a simplified method for processing and evaluating data gathered from an inhaler.

SUMMARY OF THE INVENTION

These objects are achieved by an electronic system comprising the features of claim 1. Preferred embodiments are set out in the dependent claims.

According to the present invention the evaluation unit is configured to identify the gathered data as wireless, acoustic, visual or manual input data, identify the inhaler model from which the data was gathered across different manufactures, process and evaluate the gathered data and visualize the processed data on the display.

The electronic system according to the present invention enables transmittance of data from all established and foreseeable inhalers to one single electronic system. Moreover, the electronic system allows processing and evaluation of the gathered data and thus the administration of the gathered data. Consequently, the patient is able to monitor and administer his/her data in one single electronic system, no matter which model of inhaler is used and no matter of the manufacturer of the inhaler.

In connection with the present invention the term "inhaler" is understood as being related to inhalers having no electronics installed therein but a mechanical doses counter, a Quantum® can or a nose emitting portion or, if the noise created during usage is sufficiently specific, even no such additional component or structure. The term "inhaler" is further understood as being related to inhalers which include embedded electronics, such as an electronic doses counter and/or a transmitter to wirelessly transmit data, and inhalers having an add-on device mounted thereon, the add-on device being capable to sense and transmit data relating to the number of dispensed doses and the usage of the inhaler or being capable to create a sound which can be captured by the electronic device.

Moreover, in connection with the present invention the terms "patient" and "user" are used as synonyms and are thus interchangeable.

Preferably the identification of the inhaler model may be accomplished depending on the type of the inhaler as follows:

In case the inhaler allows an electronic data transfer to the electronic system the identification may take place by use of a serial number which is transmitted to the electronic system. Preferably, the electronic system uses the serial number to identify the inhaler. Alternatively, the electronic system may automatically identify the model of the inhaler by comparing the serial number with data stored in an identification database.

In case visual or acoustic data is to be gathered from an inhaler the patient is preferably queried by the electronic system to select the inhaler, in particular the model of the inhaler, from a list of inhalers. The list of inhalers may be stored in the identification database. Alternatively, in case the visual data includes an image of the inhaler the inhaler model may be identified based on an evaluation of the visual data which will be described in more detail below. As a further alternative the inhaler, in particular a dry powder inhaler, may be identified by a specific noise characteristic emitted for example during inhalation of the pharmaceutical formulation or the preparation or actuation of the device. According to an embodiment of the invention the evaluation unit is further configured to process and evaluate the gathered data by generating a Type ID, which represents information regarding the type of the gathered data such as whether the gathered data is wireless, acoustic, visual or manual input data, generating a Source ID which is unique for each inhaler model and by which each inhaler model is identifiable, generating a timestamp representing information when a dose has been administered or the data has been received by the evaluation unit and generating an incremental dose count representing information regarding the number of doses dispensed since the previous timestamp. By using characteristic numbers such as a Type ID, a Source ID, a timestamp and/or an incremental dose count the gathered data of different inhalers is prepared in such a way that the data is comparable. In doing so data gathered from different inhaler manufacturers may be harmonized which enables easy evaluation and monitoring of the data.

In connection with the present invention the term "generating" is understood as creating characteristic numbers such as a Type ID, a Source ID, a timestamp and/or an incremental dose count based on information included in the gathered data. However, the term "generating" does also include adopting existing information contained in the gathered data as a characteristic number. For example in case data is wirelessly transferred from an inhaler the data may include a serial number of the inhaler which may be adopted by the evaluation unit as a Source ID.

According to another embodiment of the invention the evaluation unit is further configured to process and evaluate the data by generating dose quality details, representing information regarding a quality of the dose administration. Dose quality details form additional characteristic numbers to evaluate the proper use of an inhaler. In connection with the present invention the term "dose quality details" is understood as a measure in particular of the ability of the patient to inhale the prescribed amount of the pharmaceutical formulation. Studies have shown that a lack of hand-breath coordination (press and breathe), an incorrect speed and/or depth of inhalation, an incorrect actuation of the canister and a missing breath-hold after inhalation of the dose of medicament are the most frequent errors when using an inhaler. Thus, the dose quality details form characteristic numbers of how well a patient has used the inhaler in terms of the above described criteria in order to inhale the prescribed amount of the pharmaceutical formulation. In order to generate dose quality details the gathered data preferably includes the corresponding information and the inhaler from which dose quality details are to be gathered has to be equipped accordingly.

Accordingly, in connection with the present invention the term "quality of the dose administration" is understood as how well a patient has inhaled the administered does of medicament in terms of the following criteria: (i) hand-breath coordination (press and breathe), (ii) speed and/or depth of inhalation, (iii) correct actuation of the canister and (iv) sufficient breath-hold (e.g. 10 seconds) after inhalation of the dose of medicament. Thus, the quality of the dose administration is considered high when the patient meets the above criteria. Accordingly, the quality is poor if the patient does not fulfill the above criteria at all. Optionally, reference values for the above criteria, e.g. tolerance time in hand-breath coordination, a correct inhalation speed and duration of inhalation as well as an duration for breath hold, may be for example stored in a prescription database which may be accessed by the evaluation unit. The evaluation unit may compare the reference values with the data gathered from the inhaler and may thus determine a quality of the dose administration and/or dose quality details.

According to another embodiment the electronic system further comprises a storage database in which the processed data is stored as a data package, each data package comprising at least the Type ID, the Source ID, the timestamp and the incremental dose count. The database allows an easy evaluation of the data as well as the comparison of data gathered from different inhalers of different manufacturers.

Optionally, each data package further comprises the dose quality details. The storage of dose quality details as characteristic numbers in the storage database allows an advanced evaluation of the gathered data.

In connection with the present invention it has been found that the accuracy of the gathered data and thus the quality of the data differs between different data sources such as wireless, audio or visual etc. For example data from an eMDI which is received via the wireless interface preferably includes the number of dispensed doses but also a timestamp for each dose, namely the date and time when the dose has been dispensed. Contrary hereto data which is for example received via the visual interface may contain the number of multiple doses which have been dispensed over a certain time period, wherein the date and time when the gathered visual data is received by the electronic device is used to generate a timestamp. Consequently, the accuracy and thus the quality of the visual data is normally worse than of the wireless data. It therefore appears to be helpful to additionally generate a quality ID which represents the accuracy/quality of the gathered data. The quality ID may also be stored for each data package in the storage database and may be outputted and displayed to the patient. Moreover, quality of the data can be increased. One way to increase the quality of the gathered visual data may for example to additionally query the patient to manually enter the date and time when each of the doses have been dispensed. Moreover, additionally algorithms may be used to automatically increase the quality of gathered data by considering additional data of the patient such as acceleration of the inhaler or the motion profile of the patient or past adherence profiles of the patient. This way timestamps for each dose can be calculated with respective uncertainty.

In an embodiment of the invention the evaluation unit is further configured to evaluate the gathered data by summing up all of the incremented dose counts stored in combination with one or more Source IDs and stored in combination with timestamps which fall within a given time interval in order to generate usage data. Preferably, one way in which the gathered data may be used is to compile a Compliance Metric from an Average Usage Data. Average Usage Data within a predefined time range for each inhaler may be computed by summing all of the Incremental Dose Counts in entries where the Source ID matches the inhaler or medicine and where the timestamp for the entry falls in the predefined time range. Preferably, the resulting adjusted sum of Incremental Dose Counts may then be divided by the duration of the time range to provide an Average Usage figure. This Average Usage figure is a dose rate in units of Number of Doses per Unit Time, where Unit Time may be in days, weeks, months, years, or any other convenient unit of time. In these calculations, also data, e.g. timestamps and incremental dose counts, of which the quality has been increased can be included.

According to another embodiment of the invention the system further comprises a prescription database in which prescription data such as a prescribed number of administered doses over a given time interval is stored for each Source ID. Preferably, physicians may access the prescription database in order to define the exact number of doses to be dispensed for each patient individually.

According to an embodiment of the invention the evaluation unit is further configured to evaluate the gathered data by compiling compliance metrics by comparing the usage data with prescription data stored in the prescription database, wherein the usage data and the prescription data to be compared are related to the same one or more Source IDs. Preferably, in order to calculate one type of Compliance Metric from Average Usage Data, the Average Usage Data for all of the inhalers that trace to a specific prescription are summed together and compared with the prescribed usage. Optionally the summed up Average Usage Data is divided by the prescribed usage.

The prescription data may also contain information whether more than one inhaler was prescribed to a patient and which of the inhaler is used in regular intervals as a controller medication and which of the inhaler is used in case of an emergency, e.g. in case of an asthma attack, as a rescue medication. Accordingly, the usage data may contain usage information regarding usage of both of the inhalers containing controller or rescue medication. The usage data of the inhaler containing rescue medication may be used to output the number of rescue doses dispensed by this inhaler to the patient. In case multiple inhalers were prescribed to one patient the usage data and the prescription data to be compared in order to calculate Compliance Metrics are related to multiple Source IDs. The serial number and/or the Source ID of the corresponding inhaler may be used to unambiguously identify the inhaler.

Preferably, the usage data of the inhaler containing rescue medication is used to define a Health-Status of the patient. Depending on the number of times at which doses have been dispensed by the inhaler containing rescue medication in a certain time interval conclusions can be drawn regarding how often the patient had asthma attacks or was close to an asthma attack. The number of asthma attacks in a certain time interval may then be used to calculate a key figure which represents the Health-Status of a patient. A high number of asthma attacks in a certain time interval may correlate to a poor Health-Status whereas a low number of asthma attacks may correlate to a good Health-Status. The Health-Status may be output to the patient. Additionally or alternatively, the lung volume or comparable measures measured during inhalation of a pharmaceutical formulation by the patient may be used to define the Health-Status. A small lung volume may correlate to a poor Health-Status whereas a high lug volume may correlate to a good Health-Status. In order to measure the lung volume or comparable measures the inhaler to be used by the patient can for example be equipped with a flow rate sensor which is able to measure the inhalation flow of a patient during inhalation.

Additional data from additional external devices may also be used to define the Health-Status of a patient. Such additional devices may be for example a wheezmeter which analysis the wheezing of a patient due to asthma.

Preferably the usage data and/or the prescription data may contain information regarding additional devices used by the patient to administer medication such as syringes.

According to another embodiment of the invention the electronic device comprises the evaluation unit or is connectable thereto. Preferably, the electronic device is a mobile and the evaluation unit is an app stored on and executed by the mobile. The storage database, the prescription database and the identification database may be stored on the mobile but may alternatively be stored on a remote server, wherein the mobile and the remote server are wirelessly connected. Optionally the above mentioned databases are stored on multiple servers or are stored each on a different server.

According to another embodiment the electronic system comprises a server on which the evaluation unit is stored. Preferably, the electronic device is a mobile which is configured to connect to the evaluation unit and transmit data thereto or to receive data therefrom. The storage database, the prescription database and the identification database may be stored on the server together with the evaluation unit. Optionally the databases may be stored on additional servers. Optionally, the server comprises the display for visualizing processed data. The display may also be part of any other device such as a remote desktop computer or a remote mobile which is connected to the server and/or the electronic device. For example a physician may have access to a remote computer which is connected to the evaluation unit. The remote computer may comprise a display for visualizing processed data which can be viewed by the physician.

According to one embodiment of the invention the inhaler is a metered dose inhaler, a dry powder inhaler or a soft mist inhaler. As mentioned above the term "inhaler" is understood in connection with the present invention to also include inhaler with add-on devices which for example enable the inhaler to sense and transmit data of the inhaler.

According to an embodiment of the invention the medicament reservoir is a canister, a blister strip or a capsule. Canisters are preferably used in combination with metered dose inhaler and soft mist inhaler. Blister strips or capsules are preferably used in combination with dry powder inhalers (DPI).

In another embodiment of the invention the evaluation unit is configured to identify the model of the inhaler based on the gathered visual data, wherein the inhaler is identified by its form and/or color, and configured to process and evaluate the gathered data by reading out counter indica of a mechanical dose counter of the inhaler from the gathered visual data. Preferably, in case the electronic device is a mobile the patient takes a picture of the inhaler and transmits it to the evaluation unit.

According to another embodiment of the invention the electronic system further comprises an identification database in which data allowing identification of the model of the inhaler of different manufacturers is stored, wherein the evaluation unit is configured to assess the identification database and identify the model of the inhaler based on a comparison of the gathered data with the data stored in the identification database. For example, the data stored in the identification database may comprise visual characteristic based on which an inhaler may be identified, for example color, size, form and/or a serial number.

According to another embodiment of the invention the evaluation unit comprises system specific data management units which are each configured to pre-process data of the inhaler of the corresponding manufacturer wherein the evaluation unit is configured to generate the Type ID, the Source ID, the timestamp and the incremental dose count based on the pre-processed data of the manufacturer specific data management units.

In connection with the present invention the term "system specific data management units" is understood as any existing app or platform of a platform operator which differs from the applicant of the present invention, wherein the app or platform is integrated into the evaluation unit. Such a different app or platform may be the above described BreatheSmart® app and/or platform of Cohero Health. The BreatheSmart® app may be integrated as a system specific data management unit into the evaluation unit and may pre-process data received from inhalers which are operable in connection with the BreatheSmart® platform. These pre-processed data may then be further processed and evaluated by the evaluation unit according to the present invention.

In an embodiment of the invention the system specific data management units are configured to store the pre-processed data in a manufacturer specific database, wherein the evaluation unit is configured to access the system specific database and retrieve the pre-processed data therefrom. Optionally, the system specific database may be stored on a server which is controlled by a platform operator also controlling the system specific data management units.

The above objects are also achieved by a method for processing and evaluating data gathered from an inhaler which is configured to dispense doses of a pharmaceutical formulation stored in a medicament reservoir. The method comprises the steps of providing an electronic system according to the present invention, gathering the data of the inhaler via the wireless interface, the input interface and the acoustic or visual interface, identifying the gathered data as wireless, acoustic, visual or manual input data, identifying the inhaler from which the data was gathered across different manufactures, processing and evaluating the gathered data and visualizing the processed data on the display.

BRIEF DESCRIPTION OF THE FIGURES

The invention will now be described in connection with exemplary embodiments shown in the Figures in which:

FIG. 1 shows an electronic system 1 comprising an electronic device formed as a mobile 2 for gathering data from an inhaler 3 which is configured to dispense doses of a pharmaceutical formulation stored in a medicament reservoir. The inhaler 3 might be a metered dose inhaler, a dry powder inhaler or a soft mist inhaler. The metered dose inhaler might be an inhaler having a mechanical dose counter or an electronic dose counter. In case of an electronic dose counter the metered dose inhaler is an electronic metered dose inhaler (eMDI) comprising embedded electronics or an inhaler having an add-on device mounted thereon and being capable of wirelessly transmitting data of the inhaler regarding the number of dispensed or remaining doses. The medicament reservoir might be a canister, a blister strip or a capsule depending on the kind of inhaler.

Figure 1:
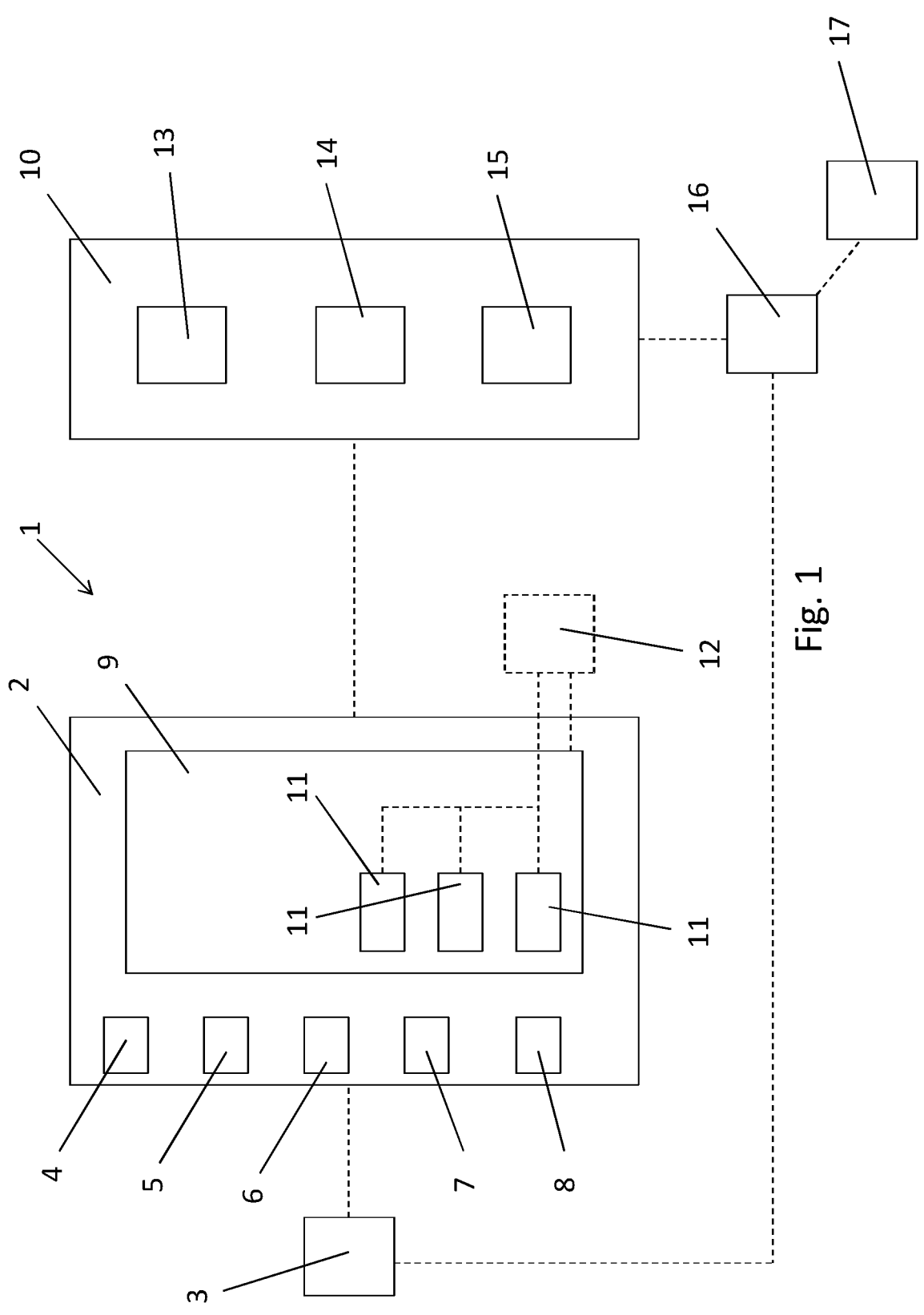
FIG. 1 shows a schematic view of the electronic system according to the present invention.

The mobile 2 comprises a wireless interface 4 such as a Bluetooth or wireless-Lan-interface for receiving wireless data from the inhaler 3 via a wireless connection, an input interface 5 such as a keyboard or touch screen for receiving manual input data, an acoustic interface 6 such as a microphone for receiving acoustic data, a visual interface 7 such as a camera for receiving visual data of the inhaler and a display 8.

The electronic system 1 further comprises an evaluation unit 9 which is configured to receive and evaluate the gathered data in order to determine adherence to prescription data and/or to determine the number of doses having been dispensed or remaining in the inhaler 3. Preferably the mobile 2 comprises the evaluation unit 9, in particular the evaluation 9 is stored on the mobile 2. The evaluation unit 9 may be an app running on the mobile 2. Alternatively the evaluation unit 9 is connected to the mobile 2. For example the evaluation unit 9 might be stored on a server 10, which is also part of the electronic system 1. The server 10 may alternatively and or additionally also comprise the display 8 for example in order to visualize processed data. The display may also be part of any other device which is connected to the server 10 and/or the mobile 2 and is part of the electronic system 1.

The evaluation unit 9 is configured to identify the gathered data as wireless, acoustic, visual or manual input data, identify the inhaler model from which the data was gathered across different manufactures, process and evaluate the gathered data and visualize the processed data on the display 8. The evaluation unit 9 is further configured to process and evaluate the gathered data by generating a Type ID, a Source ID, a timestamp, an incremental dose count and dose quality details, if available from the inhaler 3.

The Type ID represents information regarding the type of the gathered data such as whether the gathered data is wireless, acoustic, visual or manual input data. The Source ID is unique for each inhaler model and each inhaler model is identifiable by use of the Source ID. The timestamp represents information when a dose has been administered or the data has been received by the evaluation unit. The incremental dose count representing information regarding the number of doses dispensed since the previous timestamp. The dose quality details, represent information regarding a quality of the dose administration.

Optionally, the evaluation unit 9 comprises one or more system specific data management units 11 which are each configured to pre-process data of the inhaler 3 of the corresponding manufacturer wherein the evaluation unit 9 is configured to generate the Type ID, the Source ID, the timestamp and the incremental dose count based on the pre-processed data of the manufacturer specific data management units 11. Optionally, the system specific data management units 11 are configured to store the pre-processed data in a system specific database 12 (shown in FIG. 1 in dotted lines), wherein the evaluation unit 9 is configured to access the system specific database 12 and retrieve the pre-processed data there from.

The electronic system 1 further comprises a storage database in which the processed data is stored as a data package, each data package comprising the Type ID, the Source ID, the timestamp, the incremental dose count and the dose quality details if available from the inhaler 3. The electronic system 1 further comprises a prescription database 14 in which prescription data such as a prescribed number of administered doses over a given time interval is stored for each Source ID. This prescription data might be patient specific. The electronic system 1 further comprises an identification database 15 in which data allowing identification of the model of the inhaler 3 of different manufacturers is stored. All databases 13, 14, 15 are optionally stored on the server 10. However, the databases 13, 14, 15 may also be stored on different servers or may be stored on the mobile 2.

The evaluation unit 9 is configured to evaluate the gathered data by summing up all of the incremented dose counts stored in combination with one or more Source IDs and stored in combination with timestamps which fall within a given time interval in order to generate usage data. The evaluation unit 9 is further configured to evaluate the gathered data by compiling compliance metrics by comparing the usage data with prescription data stored in the prescription database, wherein the usage data and the prescription data to be compared are related to the same one or more Source IDs.

The server 10 is connected to the internet such that the data stored on the server 10, in particular the data stored in the storage database 13, the prescription database 14 and/or the identification database 15, is accessible via a cloud platform 16 by use of a remote electronic device 17 such as a remote computer or a remote mobile. The remote electronic device 17 may comprise a display which is configured to visualized processed data. Optionally, a physician may also use the cloud platform 16 in order to add or amend data stored in the prescription database 14 as well as to monitor the processed and/or evaluated data stored in the storage database 13. Optionally, in case the evaluation unit 9 is stored on the server 10 and the inhaler is capable of wirelessly transmitting data, the inhaler 3 might transmit its data directly to the evaluation unit 9 on the server 10 via the cloud platform 16 (shown in FIG. 2 by a dotted line in between the inhaler 3 and the cloud platform 16). The underlying technology for such an embodiment is for example NB-IoT or Sigfox.

In the following a method for processing and evaluating data gathered from an inhaler 3 which is configured to dispense doses of a pharmaceutical formulation stored in a medicament reservoir will be explained in connection with FIGS. 1 and 2.

In a first step an electronic system 1 as described with reference to FIG. 1 is provided. Subsequently data of the inhaler is gathered via the wireless interface, the input interface and the acoustic or visual interface. There are at least the following five possible sources from which data might be gathered:

In case the source is an electronic metered dose inhaler (eMDI) 18 the mobile 2 receives data via the wireless interface 4, such as a Bluetooth-interface. The gathered data relates amongst others to the number of doses administered and/or the number of doses remaining in the medicament reservoir, in particular a canister. The data includes a serial number by which at least the model of the inhaler is identifiable as well as timestamps for each dose administered. The timestamps provide both the date and time of the dispensed dose. Additionally, quality of dose administration is monitored and provided over the wireless communications in form of characteristic numbers.

In case the source is a generic wireless monitoring inhaler 19 such as an inhaler 3 having an add-on device mounted thereon the mobile 2 may receive the same data as already described with regard to the eMDI inhaler. However, the data received from the generic wireless monitoring inhaler 19 may differ from the data of an eMDI inhaler in that it does not include quality of dose administration.

In case the source is a visual input 20 which is gathered via the visual interface 7 such as a camera the mobile 2 receives a visual representation of either the number of doses administered by the inhaler 3 or the number of doses remaining in the medicament reservoir. The gathered data is processed and evaluated by reading out counter indica of a mechanical dose counter of the inhaler 3 from the gathered visual data. Additionally, the mobile 2 may receive a visual representation of the inhaler 3 itself, in order to identify the model of the inhaler 3 by its form and/or color.

In case the source is an audio input 21 which is gathered via the acoustic interface 6 the mobile 2 receives an audio signal indicating that a dose has been administered. The audio signal may be a whistle sound being generated by the inhaler 3 upon inhalation of a dispensed dose by the patient. However, the audio signal may also be any noise caused by the inhaler 3 which is related to the dispensing of a dose from the canister. For example the audio signal may be the sound caused by an aerosol dose streaming from the medicament reservoir towards a mouthpiece of the inhaler 3 and being inhaled by a patient.

In case the source is an user input 22 which is gathered via the input interface such as a keyboard or a touch screen of the mobile 2, the mobile 2 receives details of administered doses in either the format of individual doses having been dispensed or the total number of doses having been dispensed or remaining in the medicament reservoir. The user input may also include timestamps when each dose or the doses have been administered.

Optionally, an inhaler 3 is capable to provide multiple sources for the same dispensed dose (covering the same and/or different information). For example, an inhaler 3 is an eMDI and provides wireless data to the mobile 2 via the wireless data interface 4. Moreover, the inhaler 3 may also be capable to provide a whistle sound being generated by the inhaler 3 upon inhalation of a dispensed dose by the patient. The whistle sound is received by the mobile 2 as an audio source via the acoustic interface 6.

Figure 2:
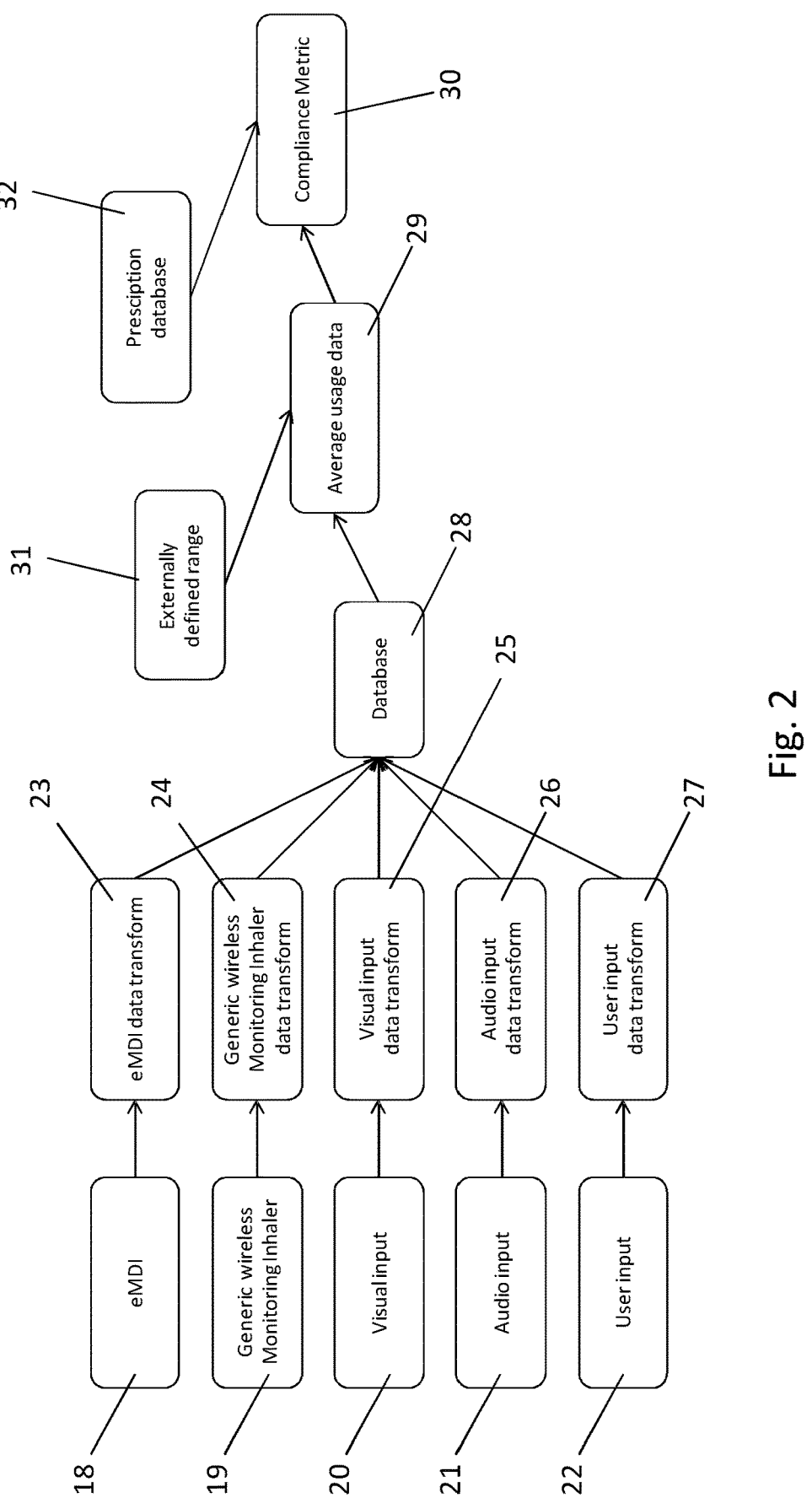
FIG. 2 shows multiple method steps of a method for processing and evaluating data gathered from an inhaler.

In order to store the gathered data in the storage database 13 and in order to allow later evaluation of the data it has to be harmonized in subsequent method steps 23 to 27 as shown in FIG. 2. Harmonization of the gathered data includes identifying the gathered data as wireless, acoustic, visual or manual input data, identifying the inhaler 3 from which the data was gathered and further processing of the gathered data. Harmonization is done by the evaluation unit 9.

Harmonization of the gathered data is accomplished by generating for each of the different inhalers 3, no matter which source as described above is used, the Type ID, the Source ID, the Timestamp, the Incremental Dose Count and the Dose Quality Details if available. Harmonization of the gathered data may differ depending on the sources from which the data is received as follows:

In case the source is an eMDI 18 or a generic wireless monitoring inhaler 19 the Type ID is set in method steps 23 and 24, respectively, to wireless as wireless data is received. Moreover, the Type ID is set to immediate Type as the timestamp of the data includes the time that dose was administered. The Source ID is set to the serial number of the eMDI 18 or the generic wireless monitoring inhaler 19. In case the source is a generic wireless monitoring inhaler 19 the user may alternatively be queried to select a model of an inhaler from a list of inhaler models stored in the identification database 15 which provides the Source ID. The Timestamp is set to the time at which the dose was provided by the eMDI 18 or the wireless monitoring inhaler 19. The Incremental Dose Count is set to 1 as each dose is entered as an immediate type data entry. The Dose Quality Details is set to key figures regarding the quality of inhalation of the dispensed dose provided by the eMDI 18. Regarding the generic wireless monitoring inhaler 19 the Dose Quality Details will be left empty as no information of the quality of inhalation is provided from the generic wireless monitoring inhaler 19.

In case the source is a visual Input 20 the Type ID is set in method step 25 to visual and to Accrued Type as the timestamp of the gathered data is the time of communicating the visual data to the mobile 2. In order to set the Source ID the evaluation unit 9 queries the user to select a model of an inhaler from a list of inhaler models stored in the identification database 15 which provides the Source ID. Alternatively, in case a visual representation of the inhaler 3 itself is included in the visual input 20 the evaluation unit 9 is configured to identify the model of the inhaler 3 by its form and/or color. In particular the evaluation unit 9 is configured to assess the identification database and identify the model of the inhaler 3 based on a comparison of the gathered data with the data stored in the identification database 15. The Timestamp is set to the current date and time when the data is received by the evaluation unit 9. The Incremental Dose Count is set to the difference between the previous reading from the corresponding inhaler and the current dose value as contained in the visual input 20. This may be applied to inhalers 3 having a dose counter that count up the dispensed doses or count down the doses remaining in the medicament reservoir as long as in the case of counting down the starting count is known. For example, the starting count may be captured from a product label located on the medicament reservoir and stored as part of the Source details in a separate sources database or in the prescription database 14. The Dose Quality Details are left empty as no information of the quality of inhalation is provided from the visual input 20.

In case the source is an Audio Input 21 the Type ID is set to Audio and to Immediate Type. Moreover, in order to set the Source ID the evaluation unit 9 queries the user to select a model of an inhaler 3 from the list stored in the identification database 15 which provides the Source ID or determines the model based on the specific sound received. The Timestamp is set to the current date and time when the data is received by the evaluation unit 9. The Incremental Dose Count is set to 1. Dose Quality Details might be available for the audio input 21.

In case the source is an User Input 22 the Type ID is set to User Input and to Accrued Type or Immediate Type, depending on whether the user input includes information when the all specific doses have been dispensed by the inhaler 3 or whether the timestamp of the gathered data is the timestamp of receiving the dispensed doses by the evaluation unit 9. In order to set the Source ID the user is queried to select the model of the inhaler 3 from the list stored in the identification database 15 which provides the Source ID. The Timestamp is set either to the current date and time when the data is entered by the user or set to a different date and time for the dose administration chosen by the user. The Incremental Dose Count is, depending on the user input, the incremental dose count or an absolute dose count that is converted to an incremental count using the same logic as used for the visual input 20 as described above. Dose Quality Details might be available for user input 22.

In method step 28 the processed data which has been processed, in particular harmonized, as described above, is stored as a data package in the storage database 13, each data package comprising the Type ID, the Source ID, the time-stamp, the incremental dose count and the does quality details if available.

Optionally, in case the gathered data has been received from one or more system specific data management units 11 of the evaluation unit 9 and has been pre-processed accordingly, the evaluation unit 9 generates the Type ID, the Source ID, the timestamp and the incremental dose count based on the pre-processed data of the manufacturer specific data management units 11 and stores the gathered data as described above in the storage database 13.

After the gathered data is harmonized and stored Average Usage Data is compiled in method step 29 and a Compliance Metric is subsequently compiled in method step 30 based on the Average Usage Data. The Average Usage Data is compiled within a predefined time range defined in method step 31. The Average usage Data is compiled for each inhaler 3 or medication type by summing up all of the Incremental Dose Counts in entries where the Source ID matches the inhaler 3 or medication type and where the Timestamp for the entry falls in the predefined time range. The resulting sum of Incremental Dose Counts is then divided by the duration of the predefined time range to provide an Average Usage figure. This Average Usage figure is a dose rate in units of Number of Doses per Unit Time, where Unit Time may be in days, weeks, months, years, or any other convenient unit of time.

To calculate one type of Compliance Metric from Average Usage Data in method step 30, the Average Usage Data for all of the inhalers 3 that are linked to a specific Prescription stored in the prescription database 14 are summed together and compared with the prescribed usage defined in the Prescription which is read out from the prescription database 14 in method step 32. For example, if two inhalers 3 are linked to one single prescription stored in the prescription database 14 and Compliance Metric is requested over a predefined time range of 8 weeks, given that an inhaler A has an Average Usage of 0.5 doses/day which is one dose every two days and inhaler B has an Average Usage of 0.33 doses/day which is one dose every three days, and the prescribed usage is one dose/day, then a Compliance Metric may be: $(0.5+0.33)/1=0.83=83\%$, so the user could be rated as 83% compliant.

This processed and evaluated data may then be visualized on the display 8.

REFERENCE NUMERALS 1 electronic system
2 mobile (electronic device)
3 inhaler
4 wireless interface
5 input interface
6 acoustic interface
7 visual interface
8 display
9 evaluation unit
10 server
11 system specific data management unit
12 system specific database
13 storage database
14 prescription database
15 identification database
16 cloud platform
17 remote electronic device
18 eMDI
19 generic wireless monitoring inhaler

20 visual input
21 audio input
22 user input
23 to 31 method steps

The invention claimed is:

1. Electronic system comprising,
an inhaler;
an electronic device for gathering data from an inhaler which is configured to dispense doses of a pharmaceutical formulation stored in a medicament reservoir, wherein the inhaler is a metered dose inhaler such as an electronic metered dose inhaler or a metered dose inhaler comprising a mechanical dose counter, a dry powder inhaler or a soft mist inhaler, an evaluation unit being configured to receive and evaluate the gathered data in order to determine adherence to prescription data and/or to determine the number of doses having been dispensed or remaining in the inhaler, and
a display for visualizing the evaluated data,
wherein the electronic device comprises,
a wireless interface for receiving wireless data from the inhaler via a wireless connection,
an input interface for receiving manual input data and an acoustic or visual interface for receiving acoustic or visual data of the inhaler,
wherein the evaluation unit is configured to:
identify the gathered data as wireless, acoustic, visual or manual input data;
process and evaluate the gathered data; and
visualize the processed data on the display;
wherein the evaluation unit is further configured to:
identify the inhaler model from which the data was gathered across different manufacturers;
wherein the identification of the inhaler model is accomplished depending on the type of the inhaler as follows:
(i) when the inhaler is an electronic metered dose inhaler the inhaler model is identified based on a serial number contained in the gathered data which is received wirelessly by the electronic device,
ii) when the inhaler is a metered dose inhaler comprising a mechanical dose counter the inhaler model is identified based on the gathered visual data, wherein the inhaler model is identified by its form, and
iii) when the inhaler is a dry powder inhaler the inhaler model is identified by a specific noise characteristic emitted during inhalation of the pharmaceutical formulation or the preparation or actuation of the device;
that the evaluation unit is further configured to process and evaluate the gathered data by:
generating a Type ID, which represents information regarding the type of the gathered data such as whether the gathered data is wireless, acoustic, visual or manual input data;
generating a Source ID which is unique for each inhaler model and by which each inhaler model is identifiable;
generating a timestamp representing information when a dose has been administered or the data has been received by the evaluation unit; and
generating an incremental dose count representing information regarding the number of doses dispensed since the previous timestamp, that the system further comprises:
an identification database in which data allowing identification of the model of the inhaler of different manufacturers is stored and
a prescription database in which prescription data such as a prescribed number of administered doses over a given time interval is stored for each Source ID,
wherein when the inhaler is an electronic metered dose inhaler the Source ID is set to the serial number of the electronic metered dose inhaler,
wherein when the inhaler is a metered dose inhaler comprising a mechanical dose counter the evaluation unit is configured to assess the identification database and identify the model of the inhaler based on a comparison of the gathered data with the data stored in the identification database which provides the Source ID,
wherein when the inhaler is a dry powder inhaler the evaluation unit queries the user to select a model of an inhaler from the list stored in the identification database which provides the Source ID or determines the model based on the specific sound received,
that the system is configured to share the data via the display to be accessed remotely by a physician and,
that the system is configured such that the physician can access the prescription database in order to modify the exact number of doses to be dispensed for each patient individually, and that the system is configured to display the modified number of doses to the patient via the display and the inhaler is configured to dispense doses of pharmaceutical formulation to the patient in accordance with the modified number of doses; and
wherein the electronic system further comprises a storage database in which the processed data is stored as a data package, each data package comprising at least the Type ID, the Source ID, the timestamp and the incremental dose count;
wherein the evaluation unit is further configured to process and evaluate the gathered data by generating a quality ID which represents the accuracy of the gathered data, wherein the accuracy depends on whether the timestamp generated by the evaluation unit represents information when a dose has been administered or whether the generated timestamp represents information when the gathered data has been received by the evaluation unit; and
wherein the quality Id is stored for each data package in the storage database and is outputted to the patient.

2. Electronic system according to claim 1, wherein the evaluation unit is further configured to evaluate the gathered data by summing up all of the incremented dose counts stored in combination with one or more Source IDs and stored in combination with timestamps which fall within a given time interval in order to generate usage data.

3. Electronic system according to claim 1, wherein the electronic device comprises the evaluation unit or is connectable thereto.

4. Electronic system according to claim 1, wherein the electronic system comprises a server on which the evaluation unit is stored.

5. Electronic system according to claim 1, wherein the medicament reservoir is a canister, a blister or a capsule.

6. Electronic system according to claim 1, wherein the evaluation unit comprises system specific data management units which are each configured to pre-process data of the inhaler of the corresponding manufacturer wherein the evaluation unit is configured to generate the Type ID, the Source ID, the timestamp and the incremental dose count based on the pre-processed data of the system specific data management units.

7. Electronic system according to claim 6, wherein the system specific data management units are configured to store the pre-processed data in a system specific database, wherein the evaluation unit is configured to access the system specific database and retrieve the pre-processed data therefrom.

8. Method for processing and evaluating data gathered from an inhaler which is configured to dispense doses of a pharmaceutical formulation stored in a medicament reservoir, the method comprising the following steps:

Providing an electronic system according to claim 1;

Gathering the data of the inhaler via the wireless interface, the input interface and the acoustic or visual interface;

Identifying the gathered data as wireless, acoustic, visual or manual input data;

Identifying the inhaler model from which the data was gathered across different manufacturers;

wherein the identification of the inhaler model is accomplished depending on the type of the inhaler as follows:

i) when the inhaler is an electronic metered dose inhaler the inhaler model is identified based on a serial number contained in the gathered data which is received wirelessly by the electronic device, ii) when the inhaler is a metered dose inhaler comprising a mechanical dose counter the inhaler model is identified based on the gathered visual data, wherein the inhaler model is identified by its form, and iii) when the inhaler is a dry powder inhaler the inhaler model is identified by a specific noise characteristic emitted during inhalation of the pharmaceutical formulation or the preparation or actuation of the device;

Processing and evaluating the gathered data; and iv) Visualizing the processed data on the display; and wherein the system is configured to share the data via the display to be accessed remotely by a physician, wherein the gathered data is processed and evaluated by:

generating a Type ID, which represents information regarding the type of the gathered data such as whether the gathered data is wireless, acoustic, visual or manual input data;

generating a Source ID which is unique for each inhaler model and by which each inhaler model is identifiable;

generating a timestamp representing information when a dose has been administered or the data has been received by the evaluation unit; and generating an incremental dose count representing information regarding the number of doses dispensed since the previous timestamp, wherein when the inhaler is an electronic metered dose inhaler the Source ID is set to the serial number of the electronic metered dose inhaler, wherein when the inhaler is a metered dose inhaler comprising a mechanical dose counter the evaluation unit is configured to assess the identification database and identify the model of the inhaler based on a comparison of the gathered data with the data stored in the identification database which provides the Source ID, wherein when the inhaler is a dry powder inhaler the evaluation unit queries the user to select a model of an inhaler from the list stored in the identification database which provides the Source ID or determines the model based on the specific sound received and, wherein the system is configured such that the physician can access the prescription database in order to modify the exact number of doses to be dispensed for each patient individually, and the system is configured to display the modified number of doses to the patient via the display, and the inhaler is configured to dispense doses of pharmaceutical formulation to the patient in accordance with the modified number of doses, the description database storing prescription data such as a prescribed number of administered doses over a given time interval for each Source ID; and wherein the electronic system further comprises a storage database in which the processed data is stored as a data package, each data package comprising at least the Type ID, the Source ID, the timestamp and the incremental dose count;

wherein the evaluation unit is further configured to process and evaluate the gathered data by generating a quality ID which represents the accuracy of the gathered data, wherein the accuracy depends on whether the timestamp generated by the evaluation unit represents information when a dose has been administered or whether the generated timestamp represents information when the gathered data has been received by the evaluation unit; and wherein the quality Id is stored for each data package in the storage database and is outputted to the patient.

9. Electronic system according to claim 1, wherein the evaluation unit is further configured to evaluate the gathered data by compiling compliance metrics by comparing the usage data with prescription data stored in the prescription database, wherein a usage data and the prescription data to be compared are related to the same one or more source IDs.

* * * * *